US00PP24613P3

(12) United States Plant Patent
Weber

(10) Patent No.: US PP24,613 P3
(45) Date of Patent: Jul. 8, 2014

(54) STRAWBERRY PLANT NAMED 'HERRIOT'

(50) Latin Name: *Fragaria×ananassa*
Varietal Denomination: Herriot

(71) Applicant: Cornell University, Ithaca, NY (US)

(72) Inventor: Courtney A. Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 111 days.

(21) Appl. No.: 13/573,626

(22) Filed: Sep. 28, 2012

(65) Prior Publication Data

US 2014/0096296 P1 Apr. 3, 2014

(51) Int. Cl.
*A01H 5/00* (2006.01)

(52) U.S. Cl.
USPC ..... Plt./209

(58) Field of Classification Search
USPC ..... Plt./209
See application file for complete search history.

*Primary Examiner* — Annette Para

(74) *Attorney, Agent, or Firm* — MacMillan, Sobanski & Todd, LLC

(57) ABSTRACT

This invention relates to a new and distinct June-bearing (short day responsive) strawberry plant named 'Herriot' primarily adapted to the growing conditions of the west central New York and other regions of similar climate. The new plant is primarily characterized by strong vigor, longer than broad fruit, conical fruit shape, uniformity in shape between primary and secondary fruit, reflexed calyx, bright red fruit color, glossy fruit skin and highly pigmented petioles.

5 Drawing Sheets

Genus and species: *Fragaria×ananassa.*
Variety denomination: 'Herriot'.

BACKGROUND AND SUMMARY OF THE INVENTION

I. Field & Utility Summary

The present invention to a new and distinct June-bearing (short day responsive) strawberry plant named 'Herriot.' Strawberry plant 'Herriot' is primarily adapted to the growing conditions of the west central New York and other regions of similar climate. The new plant is primarily characterized by strong vigor, longer than broad fruit, conical fruit shape, uniformity in shape between primary and secondary fruit, reflexed calyx, bright red fruit color, glossy fruit skin and highly pigmented petioles.

Test plantings in various locations at in New York, Illinois, Minnesota, Michigan, and Ontario, Canada have shown this plant to be widely adapted to differing soil and climactic conditions. It has shown cold hardiness typical to strawberries in a matted row system when covered with straw in the winter, which is standard procedure for this growing region.

The new plant is primarily adapted to the climate and growing conditions of west central NY, the upper mid-western U.S., the mid-Atlantic states, and southeastern Canada. This region provides the necessary winter temperatures required for it to produce a strong vigorous plant and to produce fruit in the summer harvest season from May to July, depending on location.

II. Cultivation Summary

'Herriot' originated from hand-pollinated hybridization in 1997 in Geneva, N.Y.

III. Comparisons

NYUS299, the proprietary female parent (unpatented) is June-bearing with smaller average fruit size that is medium red, firm fleshed, and conic shaped that ripens in a similar season as 'Herriot'.

'MNUS 210', the proprietary male plant, commonly known as 'Winona' in the industry (U.S. Plant Pat. No. 10,191) is June-bearing with similar fruit size that is bright red, conic shaped, moderately firm fleshed and ripens later than 'Herriot'.

The varieties which are believed to most closely resemble 'Herriot' are 'Honeoye' (not patented), 'L'Amour' (U.S. Plant Pat. No. 16,480) and 'Jewel' (U.S. Plant Pat. No. 5,897).

In comparison to the similar plant 'Honeoye', 'Herriot' differs by the following characteristics. The plant of 'Herriot' is shorter and more upright in growth habit with greater vigor. The fruit of 'Herriot' is larger than that of 'Honeoye' with a more reflexed calyx. The fruit skin and flesh color of 'Heriot' is lighter red than that of 'Honeoye'. The yield of 'Herriot' is larger than that of 'Honeoye'. The fruit of 'Herriot' is firmer with glossier skin than that of 'Honeoye'. The fruit of 'Herriot' has lower soluble solids (% Brix) and lower titratable acids than that of 'Honeoye' with lower juice pH. The harvest season of 'Herriot' is later than that of 'Honeoye' and slightly less compact.

In comparison to the similar plant, 'L'Amour', 'Herriot' differs by the following combination of characteristics. The plant of 'Herriot' is shorter and smaller with more upright leaves. The leaflets are less wide and similar in length giving them a greater length to width ratio and an ovate shape. The stipules of 'Herriot' are shorter and less wide than those of 'L'Amour'. The fruit of 'Herriot' is smaller in size, with lighter red flesh color than 'L'Amour'. The fruit of 'Herriot' has lower average soluble solids, lower titratable acids and higher juice pH than 'L'Amour'.

The flowering trusses of 'Herriot' are shorter than those of 'L'Amour'. The flowers of 'Herriot' are smaller in diameter than the flowers of 'L'Amour' with a greater petal length to width ratio than 'L'Amour'. The harvest season for 'Herriot' is more compact than that of 'L'Amour'.

In comparison to the similar plant, 'Jewel', 'Herriot' differs by the following combination of characteristics. The plant of 'Herriot' is more vigorous but with shorter stature than 'Jewel'. The foliage is smaller in size with less interveinal leaf blistering. Double petiole bracts are occasionally present in 'Herriot' and absent in 'Jewel'. The leaves are more sharply serrated in 'Herriot' than 'Jewel'. The stipules of 'Herriot' are shorter and less broad than those of 'Jewel'.

The fruit of 'Herriot' is darker red in color than 'Jewel' with more recessed seeds and a more reflexed calyx. The fruiting trusses of 'Herriot' are shorter in overall length than those of 'Jewel'. The fruit of 'Herriot' has lower soluble solids and lower titratable acidity than that of 'Jewel'.

Strawberry plant 'Herriot' has these distinguishing characteristics:

1. short plants with an upright growth habit and strong vigor;
2. predominantly trifoliate leaves with 4 and 5 leaflet leaves common with high leaf gloss and ovate leaflets with greater length than width;
3. longer than broad fruit, conical fruit shape, uniform shape between primary and secondary fruit, bright red fruit color, light red flesh color with ring of white flesh in the center and a small light red cavity, high fruit gloss and moderate flesh firmness;
4. reflexed calyx generally equal or smaller in diameter than the fruit width;
5. short pedicels and peduncles with few bracts;
6. mid-season production with high yields; and
7. compact harvest season.

IV. Breeding History

Strawberry plant 'Herriot' originated from a hand-pollinated hybridization made in 1997 in Geneva, N.Y. between NYUS299×'MNUS 210'. Both parents of 'Herriot' are hybrids of the strawberry genus of the species *Fragaria*× *ananassa*. Thus 'Herriot' is of the species *Fragaria*×*ananassa*. The seeds resulting from this controlled hybridization were germinated in a greenhouse during the winter of 1997-98. Resulting seedlings were planted in the spring of 1998 in a field in Geneva, N.Y. The seedlings fruited in the summer of 1999 and one, designated NY99-21 ('Herriot'), was selected for its early season, large, attractive, bright red fruit, strong strawberry flavor, and firm flesh.

V. Asexual Reproduction

During 1999, the original plant selection was propagated asexually by stolons (runners) at Geneva, N.Y. and a test planting of ten plants was established. Subsequently, larger test plantings have been established with asexually multiplied plants at Geneva, N.Y. The new plant was then tested over the next several years in the fruiting fields at Geneva, N.Y. Further propagation was done using tissue culture to produce disease free material for use in further testing. Tissue culture plants were used as mother plants for propagation from stolons.

VI. Stability

Asexual propagation has demonstrated that the combination of traits disclosed herein as characterizing strawberry plant 'Herriot' are fixed and remain true to type through successive generations of asexual reproduction. All propagules of strawberry plant 'Herriot' have been observed to be true to type in that during all asexual multiplication, the vegetative and fruit characteristics of the original plant have been maintained. All plants planted from dormant crowns or rooted runner tips have fruited after one season of growth in the field.

BRIEF DESCRIPTION OF THE FIGURES

The accompanying color photographs show typical specimens of the new plant at various stages of development as nearly true as it is possible to make in color reproductions. The depicted plant and plant parts were from the first harvest season, approximately 13 months after planting.

DETAILED BOTANICAL DESCRIPTION OF THE INVENTION

Figure 1A:
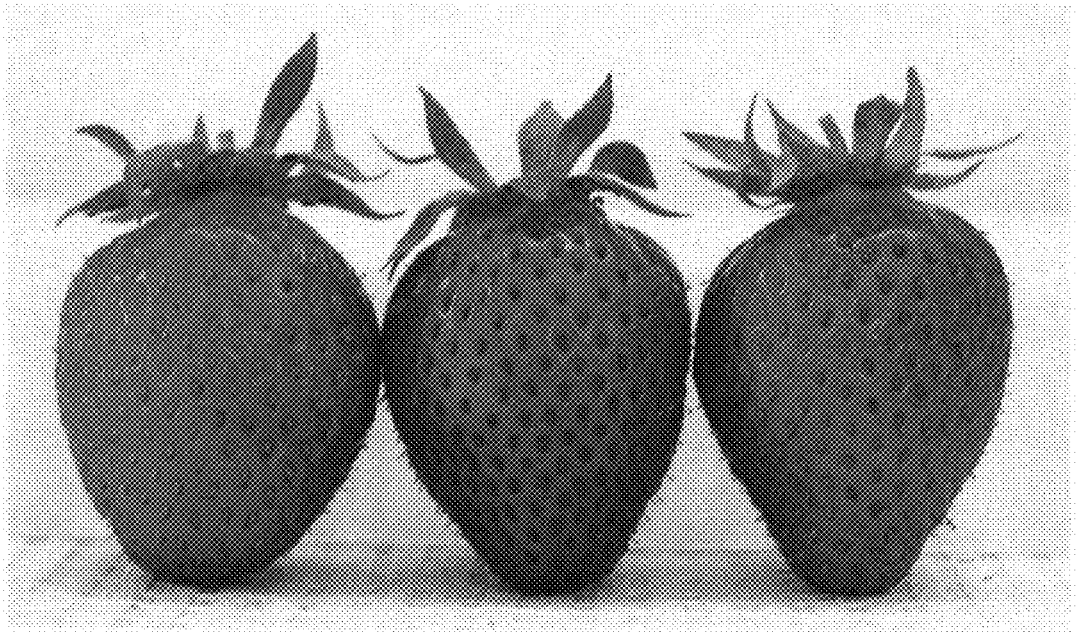
FIG. 1 shows typical external fruit characteristics of 'Herriot' (A) including calyx structure and fruit shape compared to 'Jewel' (B) on Jun. 6, 2012.
Figure 1B:
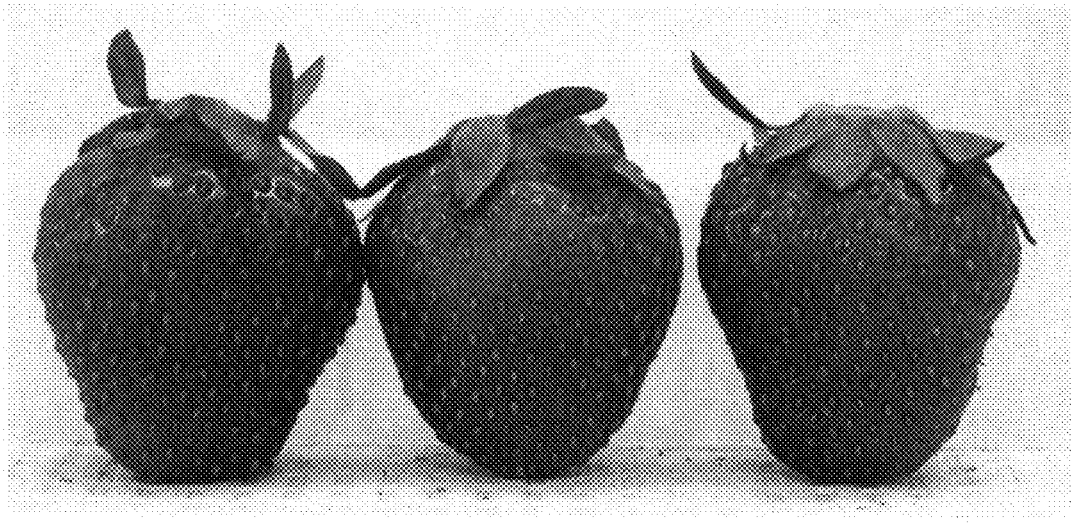
Figure 2A:
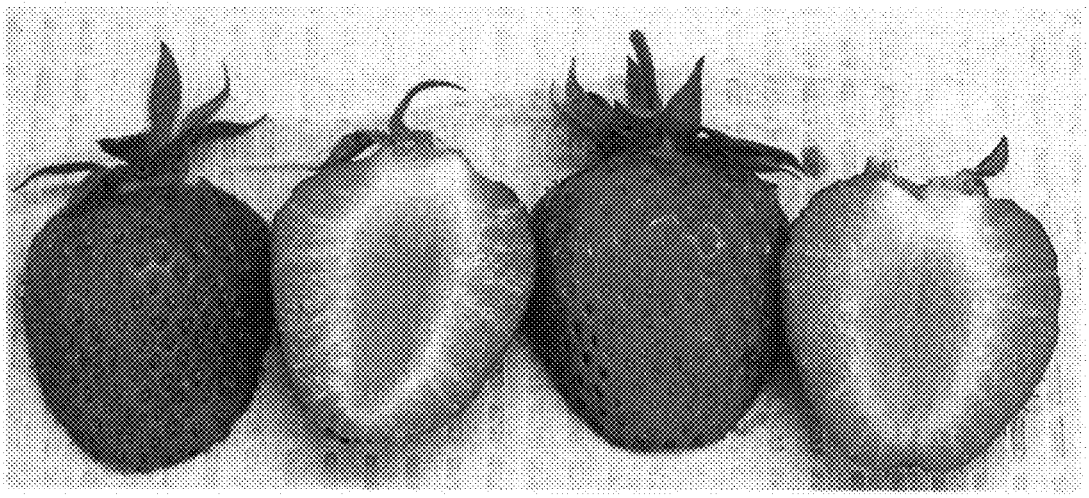
FIG. 2 shows typical internal fruit characteristics of 'Herriot' (A) compared to 'Jewel' (B) on Jun. 6, 2012.
Figure 2B:
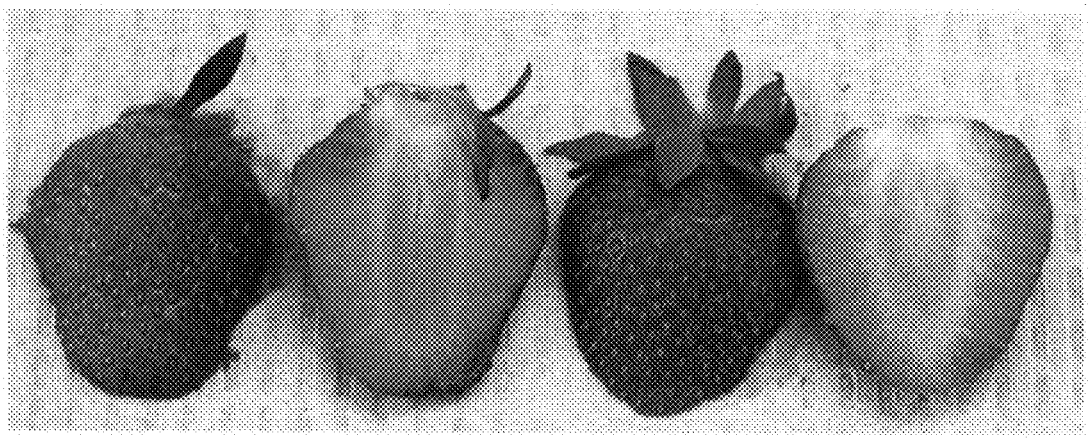
Figure 3:
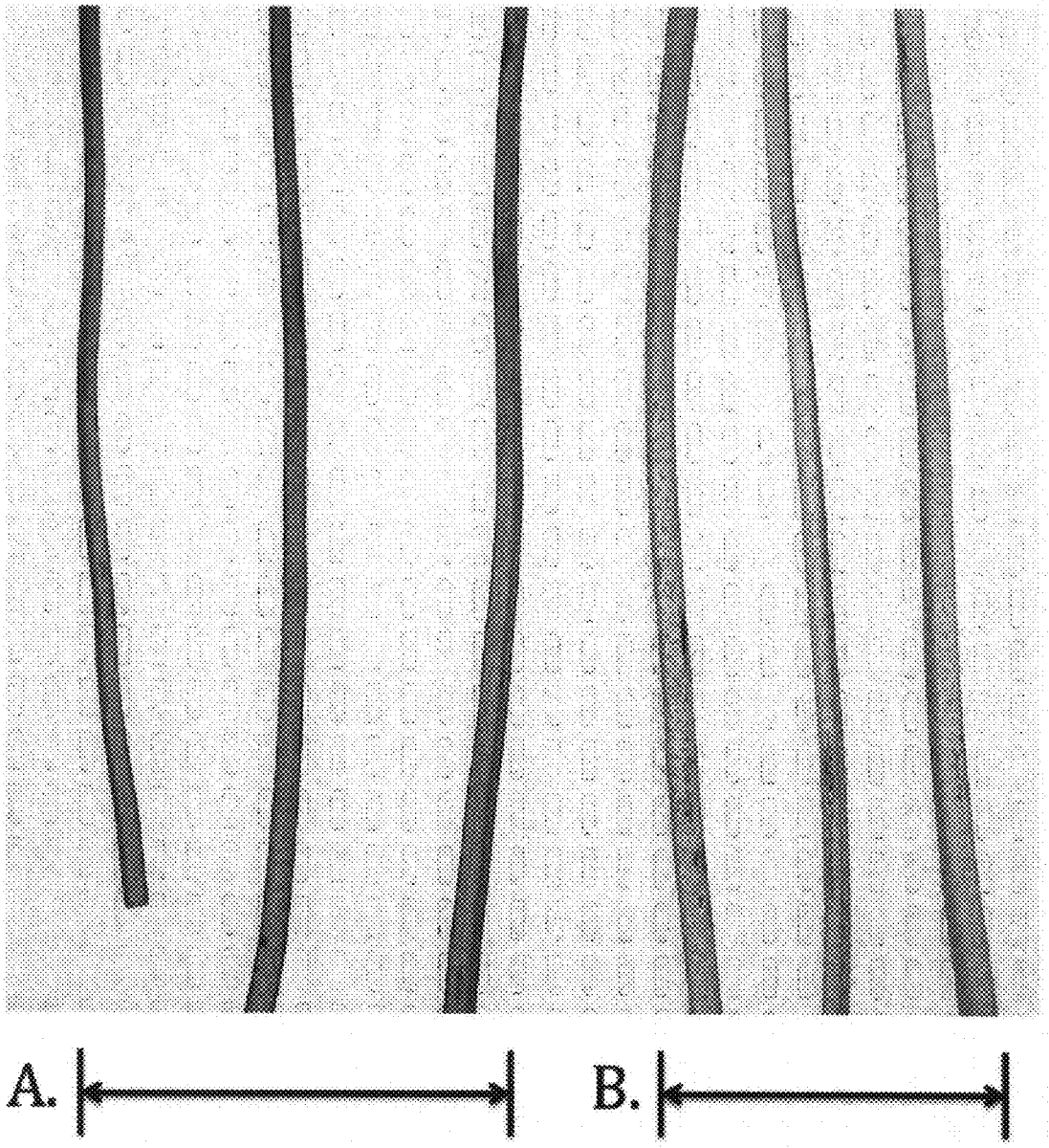
FIG. 3 shows petiole pigmentation of 'Herriot' (A-three on the left) compared to 'Jewel' (B-three on the right).
Figure 4A:
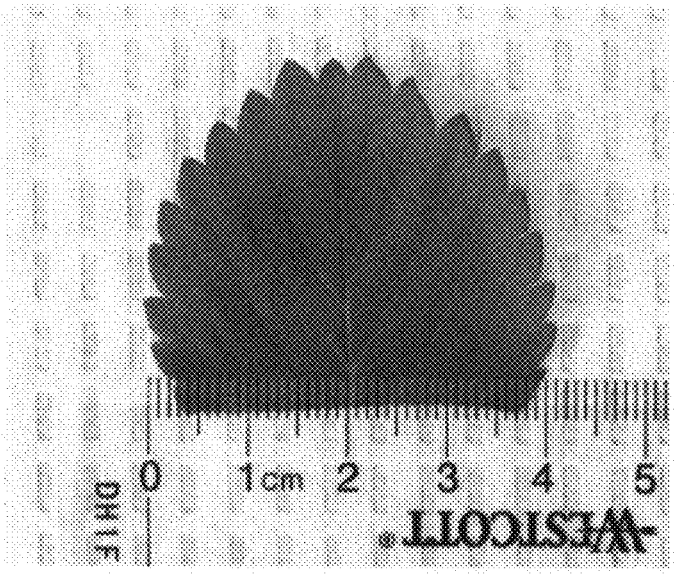
FIG. 4 shows leaf margin serrations for 'Herriot' (A), 'Jewel' (B) and 'L'Amour' (C).
Figure 4B:
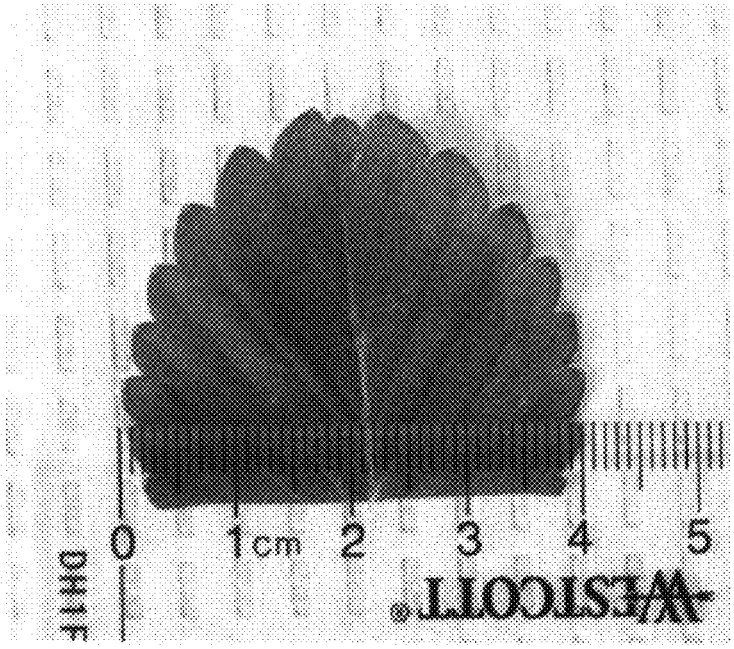
Figure 4C:
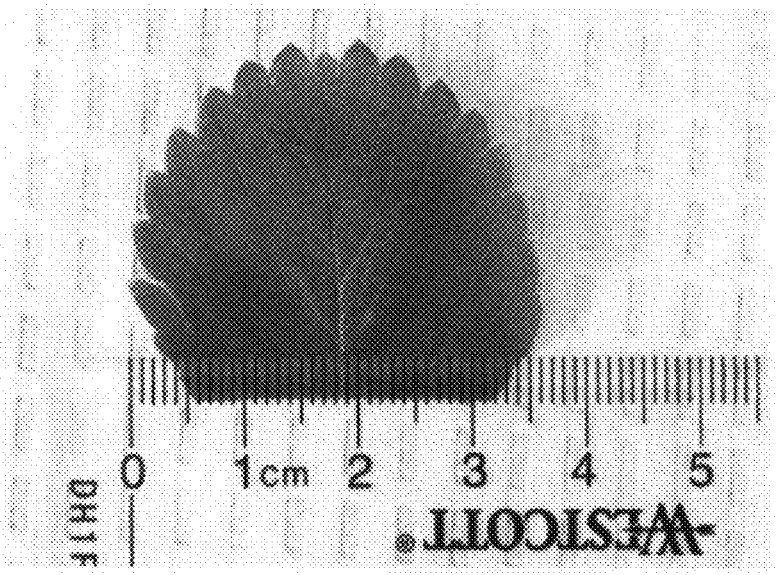

The following description of 'Herriot' unless otherwise noted, is based on observations taken during the 2012 growing season in Geneva, N.Y. These measurements and ratings were taken from plants planted in May 2011. The age of the planting is approximately 13 months and in its first harvest season. Yield observations and fruit quality characteristics are averaged from data collected during the 2003-04 and 2008-09 production seasons. The characteristics of the new plant may vary in detail, depending upon variations in environmental factors (temperature, rainfall, humidity and light intensity). 'Herriot' has not been observed under all possible environmental conditions. Color terminology where noted follows The Royal Horticultural Society Colour Chart, London.

Comparative Fruit Characteristics

'Herriot' fruit, fruit production and fruit quality characteristics. Fruit characteristics are taken from the first harvest season.

TABLE 1

Fruit characteristics: Yield

| Cultivar (kg per ha) | 2003 | 2004 | 2008 | 2009 | Average |
|---|---|---|---|---|---|
| 'Herriot'' | 8,740 | 24,790 | 4,910 | 20,010 | 14,610 |
| 'Honeoye' | 11,730 | 17,160 | 3,990 | 7,970 | 6,360 |
| 'L'Amour' | 7,090 | 14,490 | — | — | 10,790 |
| 'Jewel' | 11,160 | 15,440 | 11,270 | 5,760 | 10,910 |

Total fruit yield of 'Herriot' and similar varieties from 2 separate trials, one harvested in 2003-04 and one in 2008-09 in Geneva, NY. Fruit was harvested in June in each year. The plants of 'Herriot' and the other varieties were grown in a nursery in South Deerfield, Mass. and planted in May prior to the first harvest year for both trials.

TABLE 2

Fruit Characteristics: Weight

| Cultivar (g per berry) | 2003 | 2004 | 2008 | 2009 | Average |
|---|---|---|---|---|---|
| 'Herriot' | 10.8 | 10.6 | 10.7 | 11.2 | 10.8 |
| 'Honeoye' | 13.2 | 10.0 | 9.5 | 9.2 | 10.5 |

TABLE 2-continued

| Fruit Characteristics: Weight | | | | | |
|---|---|---|---|---|---|
| Cultivar (g per berry) | 2003 | 2004 | 2008 | 2009 | Average |
| 'L'Amour' | 11.9 | 11.7 | — | — | 11.8 |
| 'Jewel' | 10.9 | 10.6 | 11.1 | 11.1 | 10.9 |

Average fruit weight of 'Herriot' and similar varieties from 2 separate trials, one harvested in 2003-04 and one in 2008-09 in Geneva, NY. Fruit was harvested in June in each year. The plants of 'Herriot' and the other varieties were grown in a nursery in South Deerfield, Mass. and planted in May prior to the first harvest year for both trials.

TABLE 3

| Fruit Characteristics: Color | | | | |
|---|---|---|---|---|
| | Character RHS Exterior Color Mature Fruit | | | |
| | 'Herriot' red-purple 45A | 'L'Amour' red 46B | 'Jewel' red 44A | 'Honeoye' red 46A |
| Fruit Length mean (cm) | 3.70 | 4.22 | 3.46 | 3.85 |
| Fruit Width mean (cm) [1] | 3.40 | 3.62 | 3.61 | 3.55 |
| Fruit Length/ Width Ratio | 1.10 | 1.20 | 1.05 | 1.08 |
| No. Sepals/ Berry | 12.3 | 11.0 | 12.4 | 12.7 |

Comparison of secondary fruit characteristics of 'Herriot', with standards from Geneva, NY Jun. 6, 2012.
[1] Width is measured across the widest part of the berry, typically across the shoulders.

TABLE 4

| Fruit Characteristics: Quality | | | | |
|---|---|---|---|---|
| Character | 'Herriot' | 'L'Amour' | 'Jewel' | 'Honeoye' |
| Soluble solids [1,2] | 9.03 | 10.37 | 11.77 | 10.93 |
| Titratable acidity [2,3] | 9.29 | 9.64 | 10.93 | 10.89 |
| Juice pH [2] | 3.38 | 3.50 | 3.38 | 3.42 |

Comparison of 2010 fruit quality characteristics and soluble solids (% Brix), titratable acidity and juice pH of 'Herriot', with standards from Geneva, NY.
[1] soluble solids is estimated from % Brix with % Brix being an indirect measurement of the sugar content in the fruit
[2] Averaged from 3 samples on 3 dates during the harvest season.
[3] g per L equivalents of citric acid

TABLE 5

| Fruit Characteristics: Details | |
|---|---|
| Characteristic | Description |
| Ratio of length/width | Longer than broad |
| Size | Medium to large |
| Aroma | Moderate to high |
| Predominant shape | Conical |
| Difference in shapes between primary and secondary fruit | Little to none |
| Band without achenes | Intermediate width |
| Color of mature fruit | Bright to dark red |
| Evenness of color | Very even |
| Glossiness | Strong |
| Insertion of achenes | Level to slightly recessed from surface |

TABLE 5-continued

| Fruit Characteristics: Details | |
|---|---|
| Characteristic | Description |
| Attitude of the calyx segments | Somewhat reflexed |
| Size of calyx in relation to fruit diameter | Generally equal to or smaller |
| Adherence of calyx (when fully ripe) | Strong |
| Firmness of skin | Moderately firm |
| Color of flesh | Medium red with lighter ring (red 45A to 41B). |
| Distribution of red color of the flesh | Marginal through central with white inner ring (white N155C) |
| Hollow center | Moderately to strongly expressed |
| Seed color | Medium yellow-green to dark red (yellow-green 153D to red 46B). |
| Time of flowering (50% of plants at first flower) | Medium to early |
| Time of ripening (50% of plants with first ripe fruit) | Medium to early |
| Type of bearing | Fully short day responsive |

Plant characteristics:

'Herriot' plant characteristics. Plant characteristics are taken from a fully mature mid-season plant.

TABLE 6

| Plant Characteristics: Comparisons | | | |
|---|---|---|---|
| Character | 'Herriot' | 'L'Amour' | 'Jewel' |
| Plant Height mean (cm) | 21.9 | 31.9 | 27.3 |
| Vigor [1] | 8.0 | 8.3 | 5.0 |
| Canopy density [1] | 7.5 | 7.7 | 7.0 |

Comparison of plant characteristics of 'Herriot', with standards from Geneva, NY Jun. 22, 2012.
[1] Rated on a scale of 1-9 (9 being more vigorous or dense) in mature replicated plots.

TABLE 7

| Plant Characteristics: Details | |
|---|---|
| Characteristic | Description |
| Size | Medium |
| Habit | Upright |
| Density | High |
| Vigor | Strong |

Foliage Characteristics

'Herriot' foliage characteristics. Foliage characteristics are taken from a fully mature tri-foliate leaf during mid season.

TABLE 8

| Foliage Characteristics: Comparisons | | | |
|---|---|---|---|
| Character | 'Herriot' | 'L'Amour' | 'Jewel' |
| RHS Color (upper surface) | green 137A | green 137A | green 138A |
| RHS Color (lower surface) | yellow-green 148B | green 139C | green 137D |
| Terminal Leaflet Length mean (cm) | 8.3 | 8.4 | 7.5 |
| Terminal Leaflet Width mean (cm) | 7.0 | 8.5 | 7.6 |
| Terminal Leaflet ratio (L/W) | 1.18 | 0.99 | 0.99 |
| Petiole Length mean (cm) | 17.7 | 22.8 | 19.9 |

TABLE 8-continued

| Foliage Characteristics: Comparisons | | | |
|---|---|---|---|
| Character | 'Herriot' | 'L'Amour' | 'Jewel' |
| Serrations/Leaf | 26.1 | 22.3 | 18.3 |
| Stipule Length mean (cm) | 1.7 | 3.5 | 3.0 |
| Stipule Width mean (cm) | 0.4 | 0.8 | 0.8 |

Comparison of leaf characteristics of 'Herriot', with standards from Geneva, NY on Jun. 22, 2012.

TABLE 9

| Foliage Characteristics: Details | |
|---|---|
| Characteristic | Description |
| Color of upper surface | Medium to dark green |
| Color of under side | Medium to light green with yellow undertone. |
| Shape in cross section | Slightly concave |
| Interveinal blistering | Light to moderate |
| Glossiness | Moderate |
| Number of leaflets/leaf | Generally three with four or five common |
| Terminal leaflet size | Medium |
| Terminal leaflet - length/width ratio | Longer than broad |
| Terminal leaflet - shape of base | Cuneate |
| Terminal leaflet - shape serrations | Acute |
| Petiole - pubescence density | Moderate to high. |
| Petiole - stilule color | Light to medium yellow-green (yellow-green N144C) |
| Petiole - anthocyanin coloration of stipule | Little to none. |
| Petiole - attitude of hairs | Strongly outward |
| Petiole - size of bract leaflets | Small |
| Petiole - frequency of bract leaflets | Approximately 10% of the petioles |

Flower and Inflorescence Characteristics

'Herriot' inflorescence and flower characteristics. Inflorescence characteristics are taken from a fully mature plant during full bloom. Flower characteristics are taken from a secondary flower during mid season at full maturity:

TABLE 10

| Flower and Inflorescence Characteristics: Comparisons | | | |
|---|---|---|---|
| Character | 'Herriot' | 'L'Amour' | 'Jewel' |
| Fruiting Truss Length [1]mean (cm) | 14.8 | 32.3 | 20.9 |
| Corolla Diameter mean (mm) | 32 | 36 | 31 |
| Calyx Diameter mean (mm) | 32 | 33 | 34 |
| Petal Length mean (mm) | 13.8 | 15.4 | 14.0 |
| Petal Width mean (mm) | 11.8 | 13.6 | 13.3 |
| Petal L/W Ratio | 1.16 | 1.13 | 1.09 |
| Petals/Flower (mean) | 5.8 | 5.1 | 6.3 |
| Sepals/Flower (mean) | 12.3 | 11.0 | 12.4 |

Comparison of inflorescence and secondary flower characteristics of 'Herriot', with standards from Geneva, NY on May 10, 2012.
1 as measured from the base of the primary peduncle where it attaches to the crown of the plant to the furthest berry.

TABLE 11

| Inflorescence Characteristics: Details | |
|---|---|
| Characteristic | Description |
| Position relative to foliage | Above |
| Fruiting truss length | Short |

TABLE 12

| Flower Characteristics: Details | |
|---|---|
| Characteristic | Description |
| Color | White (white 155C). |
| Size | Medium to large |
| Size of calyx relative to corolla | Equal to smaller |
| Relative position of petals | Slight overlap when first fully open. |
| Petal length/width ratio | Longer than broad |
| Petal shape | Obovate |

Pest reactions: 'Herriot' is moderately resistant to the two-spotted spider mite and susceptible to aphids and flower thrips. It is resistant to leaf spot, scorch and blight. It is slightly susceptible to powdery mildew.

I claim:

1. A new and distinct strawberry plant cultivar as herein described and illustrated.

* * * * *